US009694179B2

(12) United States Patent
Platz et al.

(10) Patent No.: US 9,694,179 B2
(45) Date of Patent: Jul. 4, 2017

(54) CONNECTORIZED COCHLEAR IMPLANT SYSTEMS AND METHODS

(71) Applicant: ADVANCED BIONICS AG, Staefa (CH)

(72) Inventors: Rainer Platz, Colombier NE (CH); Lee F. Hartley, Valencia, CA (US); Lakshmi N. Mishra, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 272 days.

(21) Appl. No.: 14/424,420

(22) PCT Filed: Jul. 31, 2013

(86) PCT No.: PCT/US2013/052929
§ 371 (c)(1),
(2) Date: Feb. 26, 2015

(87) PCT Pub. No.: WO2014/035592
PCT Pub. Date: Mar. 6, 2014

(65) Prior Publication Data
US 2015/0224312 A1    Aug. 13, 2015

Related U.S. Application Data

(63) Continuation-in-part of application No. PCT/US2012/052718, filed on Aug. 28, 2012.

(51) Int. Cl.
*A61N 1/36*    (2006.01)
*A61N 1/372*    (2006.01)
(Continued)

(52) U.S. Cl.
CPC ......... *A61N 1/36032* (2013.01); *A61N 1/372* (2013.01); *A61N 1/375* (2013.01);
(Continued)

(58) Field of Classification Search
CPC ... A61N 1/05; A61N 1/08; A61N 1/36; A61N 1/06; H04R 25/00
(Continued)

(56) References Cited

U.S. PATENT DOCUMENTS 6,272,382 B1    8/2001  Faltys et al.
7,054,691 B1    5/2006  Kuzma et al.
(Continued)

FOREIGN PATENT DOCUMENTS

CN    101081188 A    12/2007
CN    101926693 A    12/2010
(Continued)

OTHER PUBLICATIONS

Communication pursuant to Article 94(3) EPC received in European Patent Application No. 12 756 060.5, dated Feb. 12, 2016.
(Continued)

*Primary Examiner* — Christopher D Koharski
*Assistant Examiner* — Roland Dinga
(74) *Attorney, Agent, or Firm* — ALG Intellectual Property, LLC (57) ABSTRACT

An exemplary system includes 1) a cochlear implant module configured to be implanted within a patient and comprising cochlear implant circuitry configured to apply electrical stimulation representative of one or more audio signals to the patient, 2) an implantable sound processor module configured to be implanted within the patient and comprising sound processor circuitry configured to optically transmit data and/or power to the cochlear implant circuitry, and 3) an optical connector assembly configured to facilitate removable coupling of the implantable sound processor module to the cochlear implant module by way of the optical connector assembly. The optical connector assembly comprises one or more optical fibers configured to facilitate the
(Continued)

optical transmission of the data and/or the power from the sound processor circuitry to the cochlear implant circuitry while the implantable sound processor module is removably coupled to the cochlear implant module by way of the optical connector assembly.

20 Claims, 7 Drawing Sheets (51) Int. Cl.
*H04R 25/00* (2006.01)
*A61N 1/375* (2006.01)

(52) U.S. Cl.
CPC ........ *A61N 1/37217* (2013.01); *H04R 25/608* (2013.01); *H04R 2460/03* (2013.01)

(58) Field of Classification Search
USPC .......................................................... 607/57
See application file for complete search history.

(56) References Cited

U.S. PATENT DOCUMENTS

| | | | | |
|---|---|---|---|---|
| 7,349,618 | B2* | 3/2008 | Nielsen | ................ A61N 1/3754 385/138 |
| 2003/0229381 | A1 | 12/2003 | Hochmair et al. | |
| 2006/0183965 | A1 | 8/2006 | Kasic, II et al. | |
| 2010/0198303 | A1* | 8/2010 | Haller | ................ A61N 1/36032 607/57 |
| 2010/0292758 | A1 | 11/2010 | Lee et al. | |
| 2011/0144719 | A1 | 6/2011 | Perkins et al. | |
| 2011/0152976 | A1 | 6/2011 | Perkins et al. | |
| 2011/0295331 | A1* | 12/2011 | Wells | ................ A61N 1/36032 607/3 |
| 2012/0197374 | A1 | 8/2012 | Vogt et al. | |
| 2015/0290458 | A1 | 10/2015 | Hartley et al. | |

FOREIGN PATENT DOCUMENTS

| | | |
|---|---|---|
| CN | 102640435 A | 8/2012 |
| CN | 104582788 A | 4/2015 |
| WO | WO-2010/028436 | 3/2010 |
| WO | WO-2010/088549 | 8/2010 |
| WO | WO-2012/106205 | 8/2012 |

OTHER PUBLICATIONS

First Office Action received in Chinese Patent Application No. 201380045209.3, dated Dec. 25, 2015.
Communication pursuant to Article 94(3) EPC received in European Patent Application No. 13745990.5, dated Jan. 29, 2016.
First Office Action received in Chinese Patent Application No. 201280075472.2, dated Jan. 15, 2016.
Non-Final Office Action received in U.S. Appl. No. 14/424,419 dated Jun. 13, 2016.
International Search Report and Written Opinion received in International Application No. PCT/US12/052718, dated May 24, 2013.
International Search Report and Written Opinion received in International Application No. PCT/US13/052929, dated Sep. 16, 2013.

* cited by examiner

CONNECTORIZED COCHLEAR IMPLANT SYSTEMS AND METHODS

RELATED APPLICATIONS

The present application claims priority to PCT International Application No. PCT/US12/52718, filed Aug. 28, 2012, the contents of which are hereby incorporated by reference in their entirety.

BACKGROUND INFORMATION

Conventional cochlear implant systems include various components configured to be implanted within a patient (e.g., a cochlear implant, an antenna, and an electrode lead) and various components configured to be located external to the patient (e.g., a sound processor, a battery, and a microphone). Unfortunately, the external components of a conventional cochlear implant system are often relatively large, bulky, and aesthetically unpleasing. Hence, various fully implantable cochlear implant systems have been described in which the sound processor and one or more other components typically located external to the patient (i.e., the battery and/or the microphone) are also implanted within the patient. In these configurations, the patient may enjoy cochlear implant functionality with little or no externally located components for various periods throughout the day.

Unfortunately, some patients cannot initially be fitted with a fully implantable cochlear implant system. For example, some patients (e.g., pediatric patients) may possess one or more physiological traits that may limit the number and/or size of components that may be implanted within their heads. Other patients may be unable to be fitted with a fully implantable cochlear implant system for technological, logistical, and/or financial reasons. Hence, these patients may be initially fitted with a conventional cochlear implant system. However, over time, they may become eligible for a fully implantable cochlear implant system. Such an upgrade would typically require a patient to undergo a surgical procedure in which all of the already implanted components of the conventional cochlear implant system are replaced with the new fully implantable cochlear implant system components. In addition to being invasive and costly, this surgical procedure could potentially cause damage to one or more of the patient's auditory structures and thereby negate any benefits that could be provided by the fully implantable cochlear implant system.

Moreover, even if a patient is initially fitted with a fully implantable cochlear implant system, it may be necessary at a future time to replace one or more components included in the fully implantable cochlear implant system. For example, it may be necessary to replace a battery and/or an implantable sound processor module included in the fully implantable cochlear implant system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Connectorized cochlear implant systems and methods are described herein. As will be described in more detail below, a connectorized cochlear implant system may include 1) a cochlear implant module configured to be implanted within a patient and comprising cochlear implant circuitry configured to apply electrical stimulation representative of one or more audio signals to the patient, 2) an implantable sound processor module configured to be implanted within the patient and comprising sound processor circuitry configured to optically transmit data and/or power to the cochlear implant circuitry, and 3) an optical connector assembly configured to facilitate removable coupling of the implantable sound processor module to the cochlear implant module by way of the optical connector assembly. The optical connector assembly may include one or more optical fibers configured to facilitate the optical transmission of the data and/or the power from the sound processor circuitry to the cochlear implant circuitry while the implantable sound processor module is removably coupled to the cochlear implant module by way of the optical connector assembly.

The systems and methods described herein may facilitate individual replacement of one or more components of a cochlear implant system after they have been implanted within a patient. For example, a patient may be initially fitted with a connectorized cochlear implant system that includes a cochlear implant module and an implantable sound processor module communicatively coupled by way of an optical connector assembly. In this particular example, the optical connector assembly is permanently coupled to the implantable sound processor module and removably connected to the cochlear implant module. After some time thereafter (e.g., in a few years), it may become desirable to replace the implantable sound processor module with a new (e.g., upgraded) sound processor module. To do so, the patient may undergo a minimally invasive surgical procedure during which the optical connector assembly is disconnected from the cochlear implant module. The implantable sound processor module and optical connector assembly may then be removed from the patient and replaced with the new implantable sound processor module (with a new optical connector assembly permanently coupled thereto that may be removably connected to the cochlear implant module). Advantageously, the remaining implanted components (i.e., the cochlear implant module and an electrode lead coupled to the cochlear implant module) may be left intact, thereby preserving their functionality and avoiding the cost and potential dangers associated with replacing them with new components as well.

As mentioned, the optical connector assemblies described herein may include one or more optical fibers configured to facilitate optical transmission of data and power from sound processor circuitry included in an implantable sound processor module to cochlear implant circuitry included in a cochlear implant module. Optical transmission (as opposed to electrical transmission) of data and power may be advantageous for many reasons. For example, it may be difficult to avoid DC current leakage (which could be harmful to the patient) with electrical transmission of data and power between sound processor circuitry included in an implantable sound processor module and cochlear implant circuitry included in a cochlear implant module due to the requirement for small geometric dimensions for an implant at the head-level. Optical transmission of data and power may obviate DC current leakage, thereby making optical transmission safer and more reliable than electrical transmission. Optical transmission may also advantageously have virtually unlimited data transmission bandwidth capabilities and may be relatively more efficient from a power transmission perspective than electrical transmission.

Figure 1:
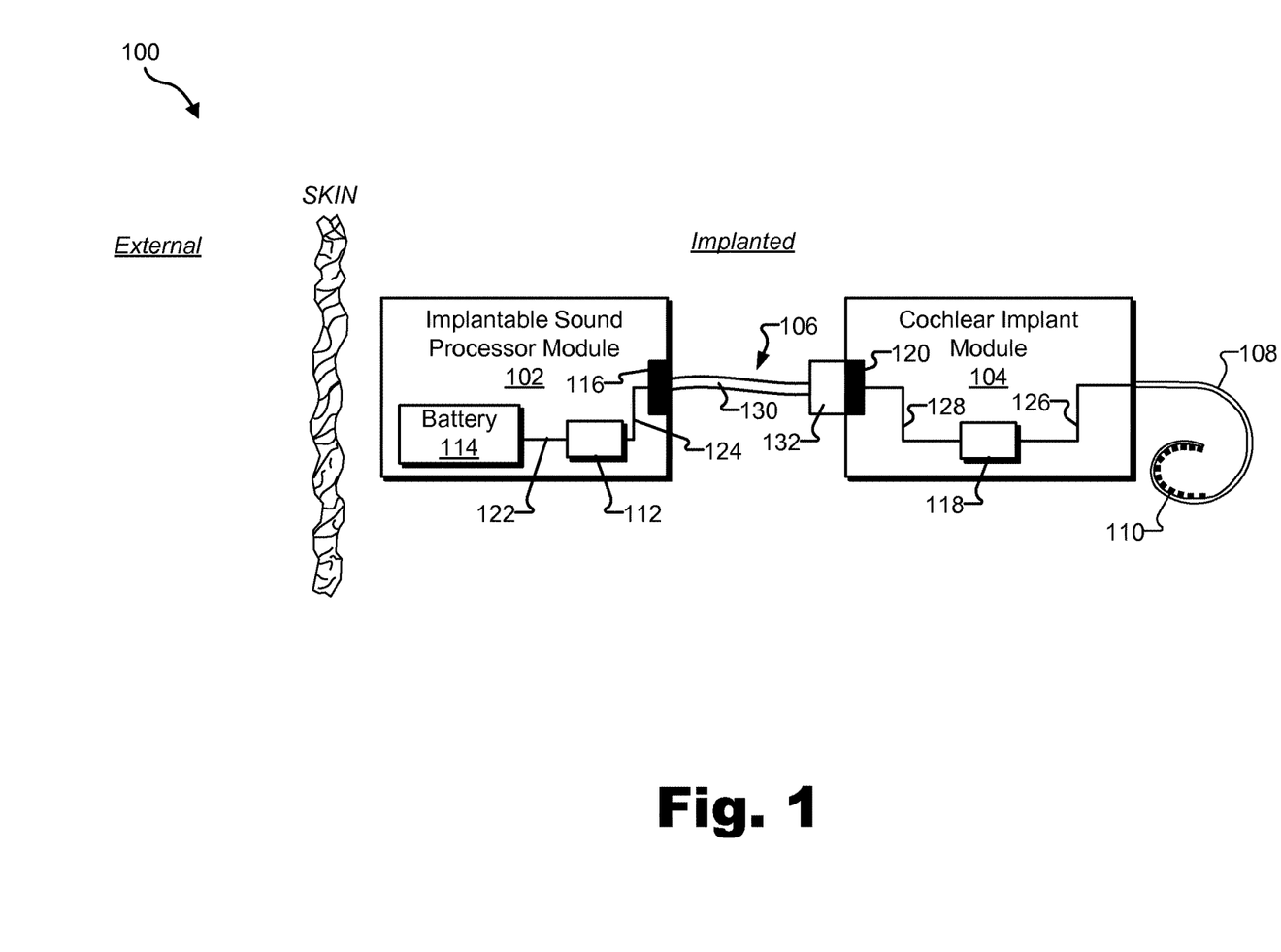
FIG. 1 illustrates an exemplary connectorized cochlear implant system according to principles described herein.

FIG. 1 illustrates an exemplary connectorized cochlear implant system 100. As shown, connectorized cochlear implant system 100 may include various components configured to be implanted within the patient. Hence, connectorized cochlear implant system 100 may be referred to as a "fully implantable cochlear implant system."

As shown, connectorized cochlear implant system 100 may include an implantable sound processor module 102, a cochlear implant module 104, an optical connector assembly 106, and a lead 108 having a plurality of electrodes 110 disposed thereon. Implantable sound processor module 102 may include any suitable housing, overmold, or case (e.g., a hermetically sealed housing) configured to house sound processor components. For example, implantable sound processor module 102 may house sound processor circuitry 112, a battery 114, and an optical feedthrough assembly 116. Cochlear implant module 102 may include any suitable housing, overmold, or case (e.g., a hermetically sealed housing) configured to house various cochlear implant components. For example, cochlear implant module 102 may house cochlear implant circuitry 118 and an optical feedthrough assembly 120. Additional or alternative components may be housed within implantable sound processor module 102 and/or cochlear implant module 104 as may serve a particular implementation.

Sound processor circuitry 112 may be configured to direct cochlear implant circuitry 118 to generate and apply electrical stimulation (also referred to herein as "stimulation current") representative of one or more audio signals (e.g., one or more audio signals detected by a microphone (not shown), input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor circuitry 112 may process the one or more audio signals in accordance with a selected sound processing strategy or program to generate appropriate stimulation parameters for controlling cochlear implant circuitry 118. As will be described below, sound processor circuitry 112 may optically transmit data (e.g., one or more stimulation parameters) to cochlear implant circuitry 118 by way of one or more optical fibers included within optical connector assembly 106.

Battery 114 may be electrically coupled to sound processor circuitry, as illustrated by connection 122. In some examples, battery 114 may provide operating power for both sound processor circuitry 112 and cochlear implant circuitry 118. As will be described below, sound processor circuitry 112 may optically transmit power provided by battery 114 to cochlear implant circuitry 118 by way of one or more optical fibers included within optical connector assembly 106.

Optical feedthrough assembly 116 may be communicatively coupled to sound processor circuitry 112 by way of a communication link 124. Communication link 124 may include any type of communication link (e.g., an optical communication link, an electrical communication link, etc.) as may serve a particular implementation. As will be described below, optical feedthrough assembly 116 may optically connect one or more optical fibers included in optical connector assembly 106 to sound processor circuitry 112, thereby facilitating optical transmission of data and power by sound processor circuitry 112 to cochlear implant circuitry 118.

Cochlear implant module 104 may be implemented by any type of implantable stimulator that may be used in association with the systems and methods described herein. For example, cochlear implant module 104 may be implemented by an implantable cochlear stimulator. In some alternative implementations, cochlear implant module 104 may be implemented by a brainstem implant and/or any other type of cochlear implant that may be implanted within a patient.

As mentioned, cochlear implant module 104 may include cochlear implant circuitry 118 and optical feedthrough assembly 120 disposed therein. Cochlear implant circuitry 118 may be configured to generate electrical stimulation representative of an audio signal processed by sound processor circuitry 112 in accordance with one or more stimulation parameters transmitted thereto by sound processor circuitry 112. Cochlear implant circuitry 118 may be further configured to apply the electrical stimulation to one or more stimulation sites within the patient via one or more electrodes 110 disposed along lead 108. In some examples, cochlear implant circuitry 118 may include a plurality of independent current sources each associated with a channel defined by one or more of electrodes 110. In this manner, different stimulation current levels may be applied to multiple stimulation sites simultaneously by way of multiple electrodes 110.

As shown, cochlear implant module 104 may be coupled to lead 108. Lead 108 may be coupled to cochlear implant module 104 in any suitable manner. For example, a proximal end of lead 108 may be integrated into or otherwise permanently coupled to cochlear implant module 104 such that the one or more wires disposed within lead 108 and associated with electrodes 110 may pass through cochlear implant module 104 to cochlear implant circuitry 118 by way of an electrical connection 126.

Optical feedthrough assembly 120 may be communicatively coupled to cochlear implant circuitry 118 by way of a communication link 128. Communication link 128 may include any type of communication link (e.g., an optical communication link, an electrical communication link, etc.) as may serve a particular implementation. As will be described below, optical feedthrough assembly 120 may optically connect one or more optical fibers included in optical connector assembly 106 to cochlear implant circuitry 118, thereby facilitating optical transmission of data and power by sound processor circuitry 112 to cochlear implant circuitry 118.

Optical connector assembly 106 may include a cable 130 and a modular connector 132 disposed at a distal end of cable 130. Cable 130 and modular connector 132 may each be made out of any suitable biocompatible material.

Figure 2:
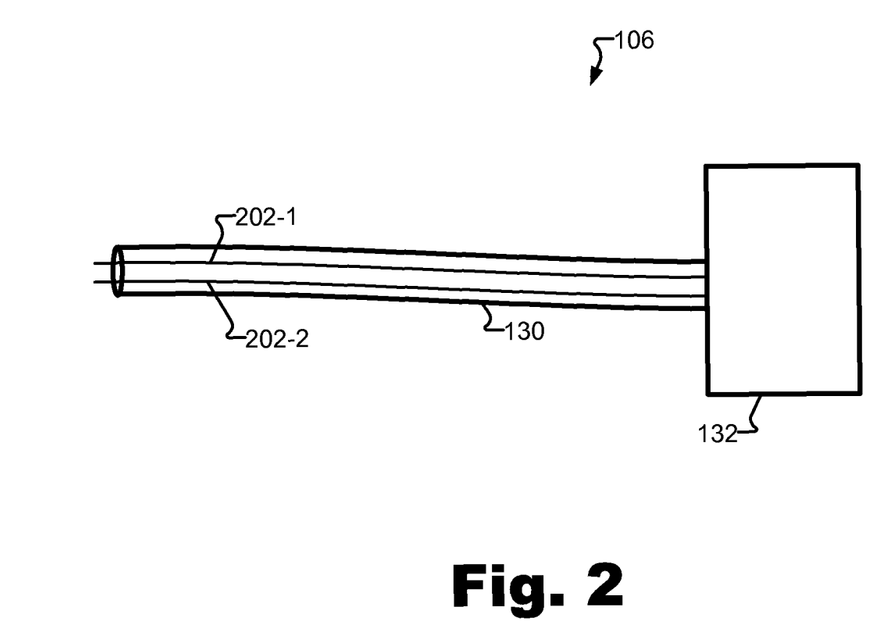
FIG. 2 shows an optical connector assembly according to principles described herein.

FIG. 2 shows optical connector assembly 106 in more detail. As shown in FIG. 2, cable 130 may house optical fibers 202-1 and 202-2 (collectively "optical fibers 202"). Two optical fibers 202 are shown as being housed within cable 130 for illustrative purposes. It will be recognized that any other number of optical fibers (e.g., only one) may be housed within cable 130 as may serve a particular implementation. One or more of optical fibers 202 may facilitate optical transmission of data and power from sound processor circuitry 112 to cochlear implant circuitry 118 while implantable sound processor module 102 is removably coupled to cochlear implant module 104 by way of optical connector assembly 106. Additionally or alternatively, one or more of optical fibers 202 may facilitate optical transmission of data (e.g., back telemetry data) from cochlear implant circuitry 118 to sound processor circuitry 112 while implantable sound processor module 102 is removably coupled to cochlear implant module 104 by way of optical connector assembly 106.

Modular connector 132 may include any type of connector configured to be removably connected to any of the modules or other suitable components described herein (e.g., cochlear implant module 104). For example, modular connector 132 may include a plug apparatus configured to plug into a corresponding receptacle associated with a module (e.g., cochlear implant module 104). The receptacle associated with the module may be integrated into the module (e.g., into an optical feedthrough assembly included within the module), coupled to a distal end of a cable connected to the module, or otherwise associated with the module. As used herein, references to modular connector 132 being "removably connected" to a particular component (e.g., cochlear implant module 104) refer to the modular connector 132 being capable of being relatively easily and/or readily disconnected (e.g., unplugged) from the particular component by a surgeon or other person in a way that does not damage either the modular connector 132 or the particular component.

Returning to FIG. 1, a proximal end of cable 130 may be permanently coupled to implantable sound processor module 102. As used herein, references to a proximal end of a cable being "permanently" coupled to a module (e.g., cable 130 to implantable sound processor module 102) refers to the proximal end of the cable being integrated into or otherwise affixed to the module such that the cable is not meant to be removed from the module by a user. In some examples, proximal end of cable 130 is permanently coupled to implantable sound processor module 102 by being permanently attached to optical feedthrough assembly 116. In this configuration, optical feedthrough assembly 116 optically connects the one or more optical fibers disposed in cable 130 to sound processor circuitry 112.

In the example of FIG. 1, modular connector 132 is configured to removably connect to cochlear implant module 104. In configurations in which modular connector 132 is removably connected to cochlear implant module 104, optical feedthrough assembly 120 optically connects the one or more optical fibers disposed in cable 130 to cochlear implant circuitry 118. Hence, in the example of FIG. 1, implantable sound processor module 102 may be removably coupled to cochlear implant module 104 by removably connecting modular connector 132 to cochlear implant module 104.

Once implantable sound processor module 102 has been removably coupled to cochlear implant module 104, sound processor circuitry 112 may optically transmit data (e.g., one or more stimulation parameters) and power (e.g., power supplied by battery 114) to cochlear implant circuitry 118. This may be done in any suitable manner. For example, the data and/or power may be optically modulated and transmitted by way of one or more optical fibers disposed within cable 130. Cochlear implant circuitry 118 may likewise transmit data back to sound processor circuitry 112 while implantable sound processor module 102 is removably coupled to cochlear implant module 104.

Figure 3:
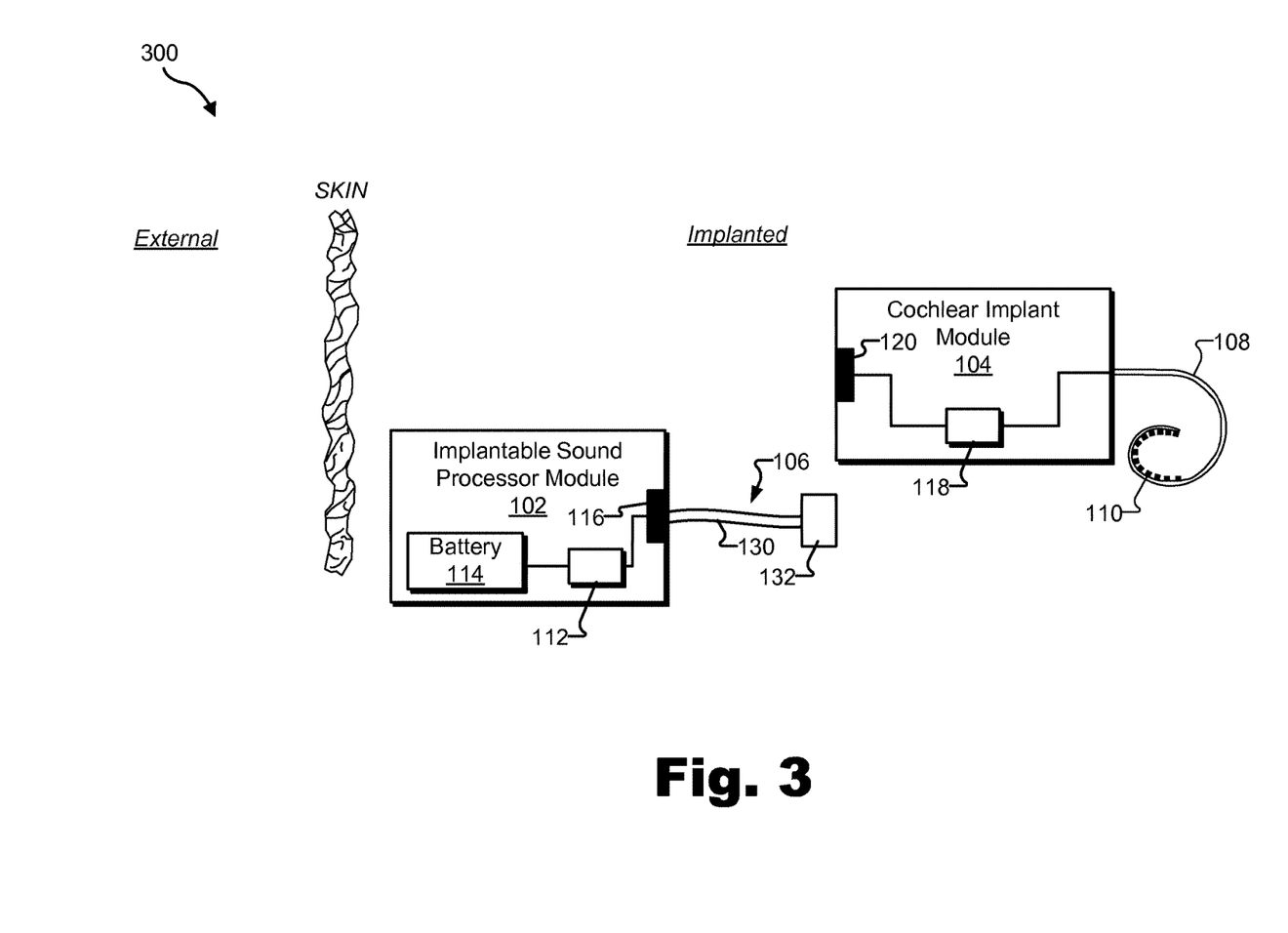
FIG. 3 shows the connectorized cochlear implant system of FIG. 1 after a modular connector has been disconnected from a cochlear implant module according to principles described herein.

To decouple implantable sound processor module 102 from cochlear implant module 104, a user may disconnect modular connector 132 from cochlear implant module 104. This may be performed in any suitable manner. FIG. 3 shows connectorized cochlear implant system 100 after modular connector 132 has been disconnected from cochlear implant module 104. As shown, implantable sound processor module 102 is no longer coupled to cochlear implant module 104. In some examples, a different component (e.g., an antenna or a different implantable sound processor module) may be coupled to cochlear implant module 104 in place of implantable sound processor module 102.

Figure 4:
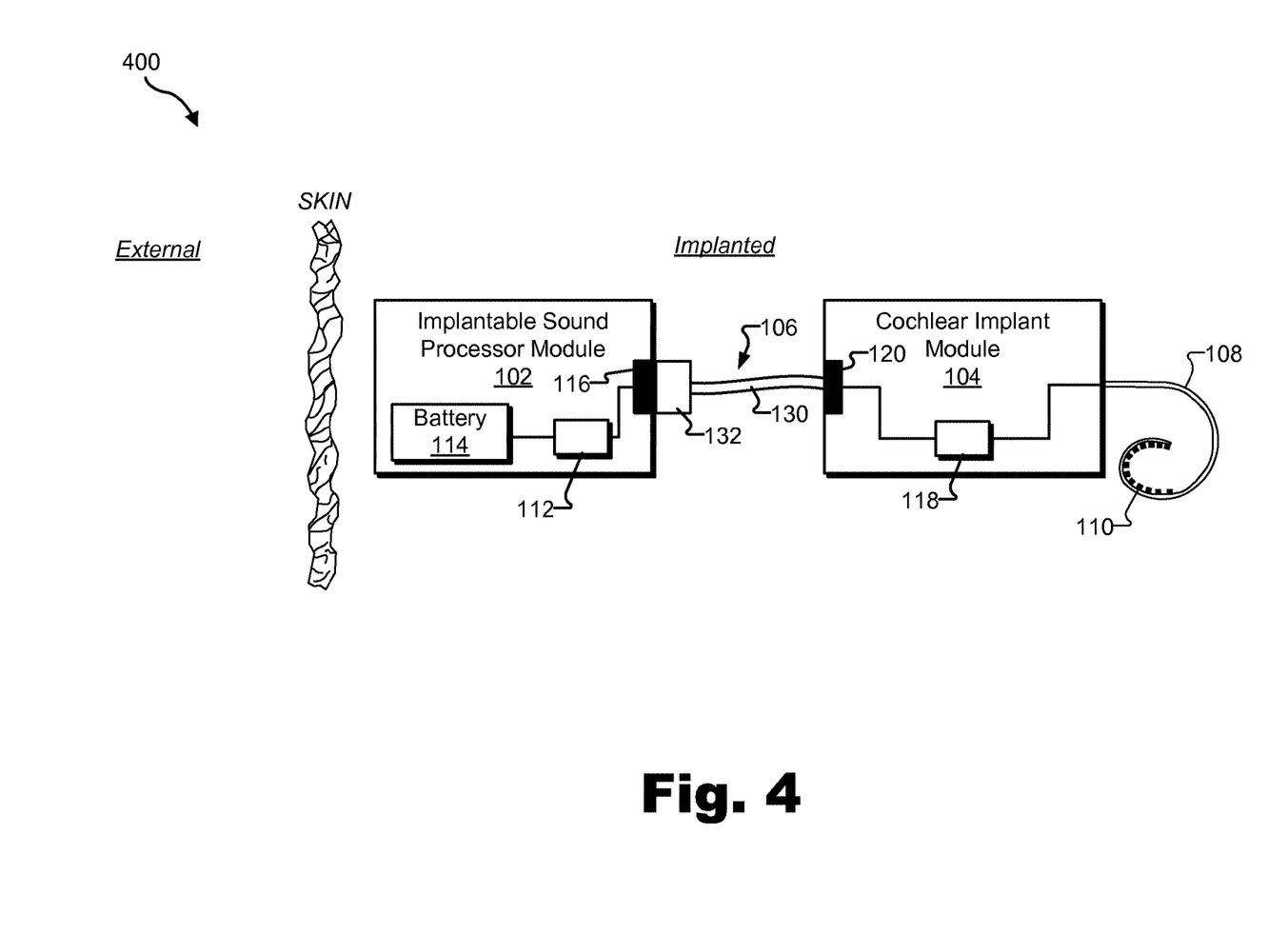
FIGS. 4-7 illustrate various exemplary connectorized cochlear implant systems according to principles described herein.

FIG. 4 illustrates another exemplary connectorized cochlear implant system 400. Connectorized cochlear implant system 400 is similar to connectorized cochlear implant system 100 in that it includes implantable sound processor module 102, cochlear implant module 104, and optical connector assembly 106. However, in connectorized cochlear implant system 400, optical connector assembly 106 (i.e., a proximal end of cable 130) is permanently coupled to cochlear implant module 104 instead of to implantable sound processor module 102. In this configuration, modular connector 132 is configured to removably connect to implantable sound processor module 102. While modular connector 132 is in a connected state (i.e., connected to implantable sound processor module 102), optical feedthrough assembly 116 optically connects the one or more optical fibers disposed in cable 130 to sound processor circuitry 112. Hence, in the example of FIG. 4, implantable sound processor module 102 may be removably coupled to cochlear implant module 104 by removably connecting modular connector 132 to implantable sound processor module 102.

Figure 5:
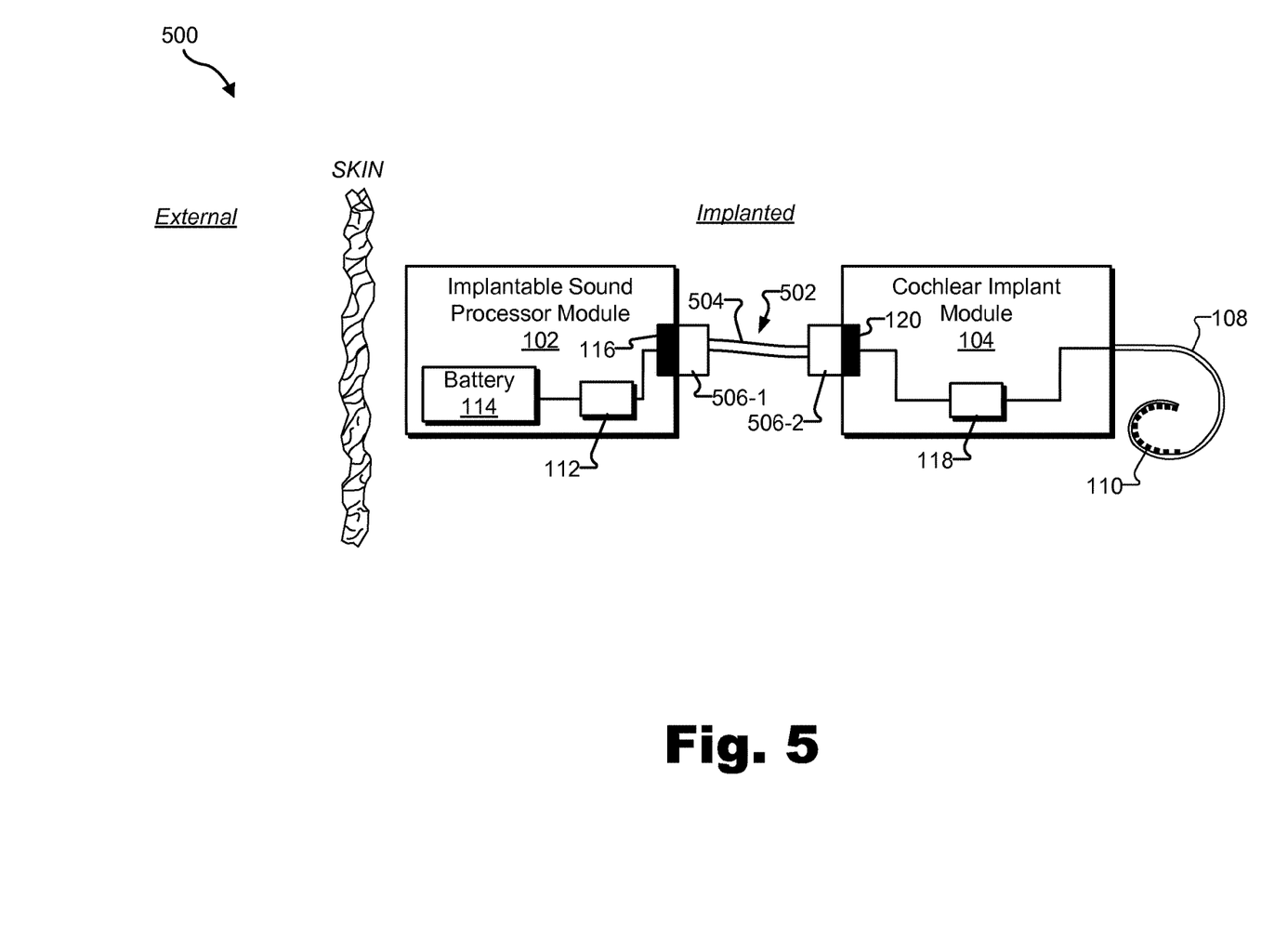

FIG. 5 illustrates another exemplary connectorized cochlear implant system 500. As shown, connectorized cochlear implant system 500 includes an optical connector assembly 502 having modular connectors 506-1 and 506-2 (collectively "modular connectors 506") disposed at both ends of a cable 504 that houses one or more optical fibers. Modular connector 506-1 is configured to removably connect to implantable sound processor module 102 and modular connector 506-2 is configured to removably connect to cochlear implant module 104. While modular connectors 506 are both in a connected state, sound processor circuitry 112 may optically transmit data and/or power to cochlear implant circuitry 118 and cochlear implant circuitry 118 may transmit data to sound processor circuitry 112.

Figure 6:
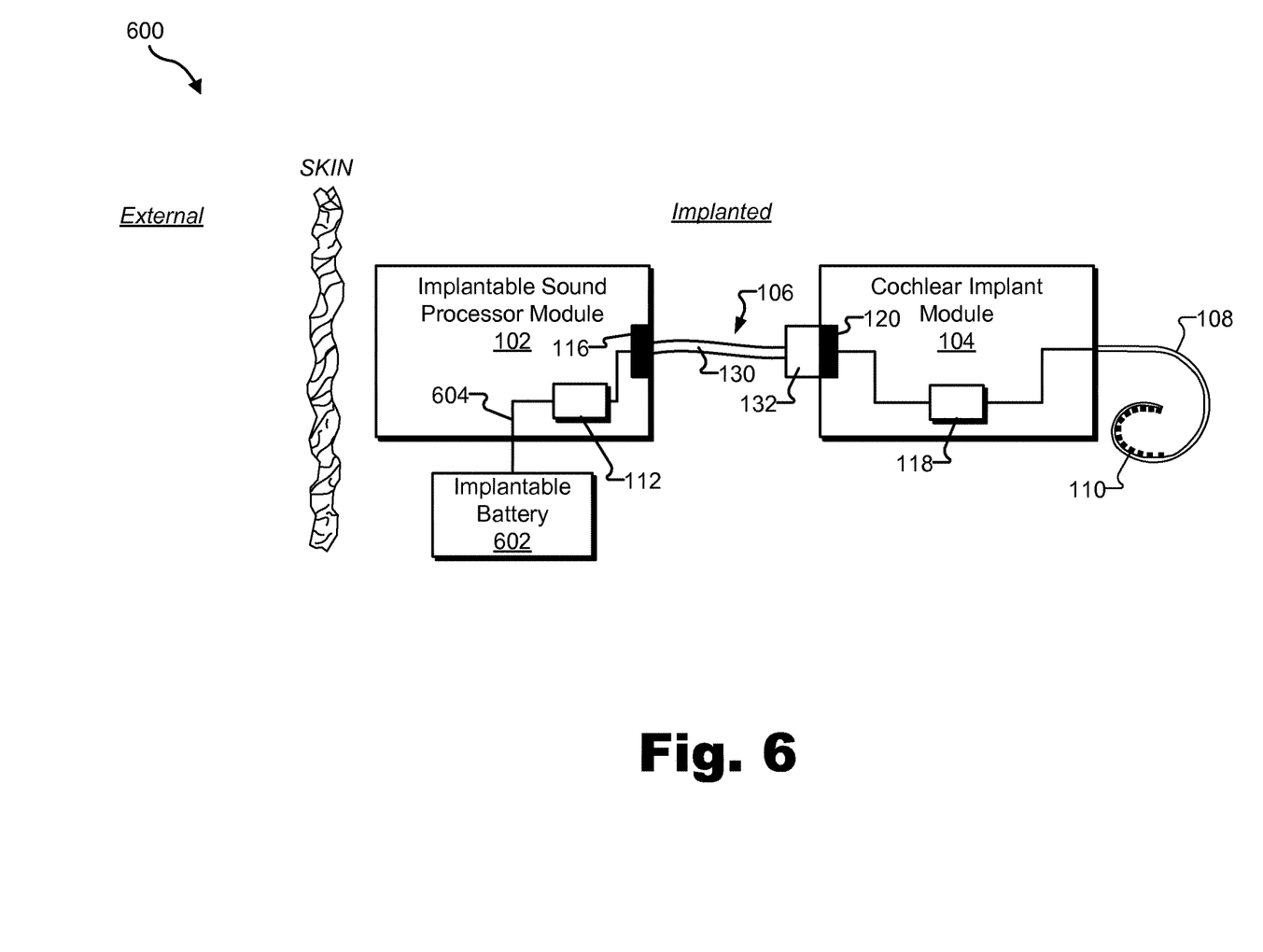

As shown in the preceding examples, battery 114 may be included within implantable sound processor module 102. In some alternative examples, battery 114 may be separate from (i.e., not included in) implantable sound processor module 102. To illustrate, FIG. 6 shows an exemplary connectorized cochlear implant system 600 in which an implantable battery 602 is located outside implantable sound processor module 102. In this configuration, implantable battery 602 may be coupled to sound processor circuitry 112 by way of a power link 604, which may include any suitable link (e.g., an electrical link, an optical link, etc.) configured to facilitate transmission of power.

In some examples, both implantable sound processor module 102 and implantable battery 602 are implanted within the head of the patient. Alternatively, implantable sound processor module 102 may be implanted within the head of the patient and implantable battery 602 may be implanted within the chest of the patient (or in any other suitable location capable of being implanted with a relatively large battery). In this case, power link 604 may be implemented by a cable and/or one or wires tunneled from the chest to the head.

As mentioned, implantable sound processor module 102 may be decoupled from cochlear implant module 104 so that another component may be removably coupled to cochlear implant module 104. For example, in some examples, it may be desirable for cochlear circuitry 118 to communicate with a sound processor located external to the patient. To this end, cochlear implant module 104 may be removably connected to an antenna configured to wirelessly communicate with the externally located sound processor.

Figure 7:
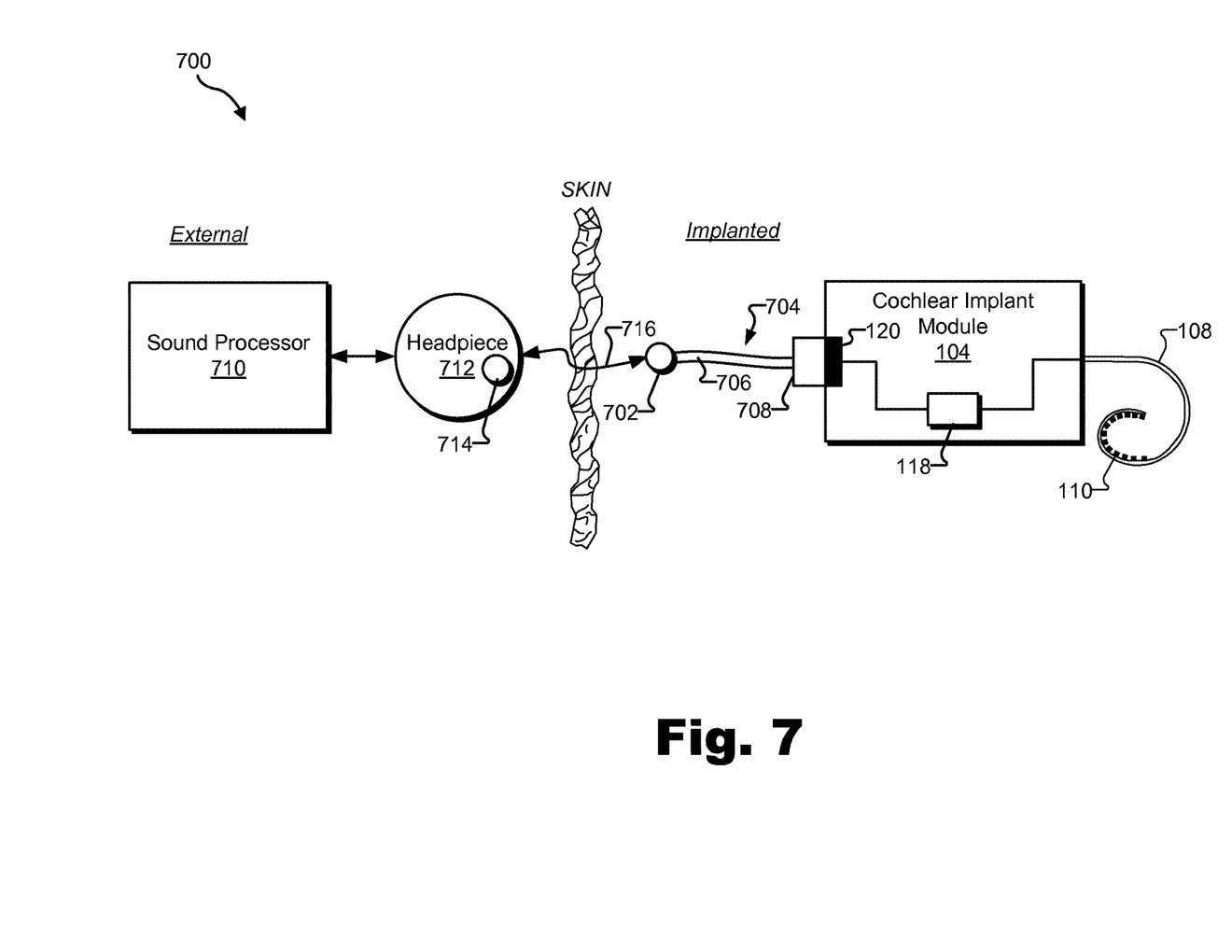

To illustrate, FIG. 7 shows an exemplary configuration 700 in which an antenna 702 (e.g., a coil and/or one or more wireless communication components) has been removably coupled to cochlear implant module 104 in place of implantable sound processor module 102. As shown, an optical connector assembly 704 having a cable 706 and a modular connector 708 is permanently coupled to antenna 702. To removably couple antenna 702 to cochlear implant module 104, modular connector 708 may be removably connected to cochlear implant module 104. In this configuration, antenna 702 is communicatively coupled to cochlear implant circuitry 118.

As shown, antenna 702 may facilitate wireless communication between an externally located sound processor 710 and cochlear implant circuitry 118. Sound processor 710 may include or be implemented by a behind-the-ear ("BTE") unit, a body worn device, an electro-acoustic stimulation ("EAS") device, and/or any other sound processing unit as may serve a particular implementation.

Sound processor 710 may be communicatively coupled to a headpiece 712, which may include an external antenna 714 (e.g., a coil and/or one or more wireless communication components). Headpiece 712 may be configured to be affixed to the patient's head and positioned such that external antenna 714 is communicatively coupled to implanted antenna 702 by way of a wireless communication link 716 (which may include a bi-directional communication link and/or one or more dedicated uni-directional communication links as may serve a particular implementation). In this configuration, data and/or power may be wirelessly transmitted between sound processor 710 and cochlear implant circuitry 118 via the wireless communication link 716.

Once implantable sound processor module 102 has been implanted, it may be activated (i.e., turned on) in any suitable manner (e.g., by utilizing any of the techniques described in WO 2011/095229 A1, which application is incorporated herein by reference in its entirety) by any suitable activation means. Likewise, implantable sound processor module 102 may be deactivated (e.g., to conserve power or for any other reason) using any of the techniques described in WO 2011/095229 A1 or in any other suitable manner.

In some examples, implantable sound processor module 102 (i.e., sound processor circuitry 112) may be configured to detect a fault in the connection of optical connector module 106 to either implantable sound processor module 102 or cochlear implant module 104 (e.g., a short or open circuit in the connection). In response, implantable sound processor module 102 may initiate a shut down procedure in which implantable sound processor module 102 safely shuts down and notifies a user of the connection fault.

In some examples, cochlear implant circuitry 118 may be configured to automatically detect that a particular component is connected to cochlear implant module 104 by way of optical connector assembly 106 and operate in accordance with a protocol corresponds to the particular component. For example, cochlear implant circuitry 118 may detect that implantable antenna 702 is connected to cochlear implant module 104, and, in response, operate in accordance with a radio frequency ("RF") inductive link communication protocol while implantable antenna 702 is connected to cochlear implant module 104. As used herein, an "RF inductive link communication protocol" refers to any suitable communication protocol that may be used to wirelessly communicate with an external sound processor (e.g., sound processor 710).

Subsequently, cochlear implant circuitry 118 may detect a disconnection of implantable antenna 702 from cochlear implant module 104 and a connection of implantable sound processor module 102 to cochlear implant module 104. In response, cochlear implant circuitry 118 may dynamically switch from operating in accordance with the RF inductive link communication protocol to operating in accordance with an optical link communication protocol while implantable sound processor module 102 is connected to cochlear implant module 104. As used herein, an "optical link communication protocol" refers to any suitable communication protocol that may be used to optically communicate with an implantable sound processor module (e.g., implantable sound processor module 102).

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a cochlear implant module configured to be implanted within a patient and comprising cochlear implant circuitry configured to apply electrical stimulation representative of one or more audio signals to the patient;
    an implantable sound processor module configured to be implanted within the patient and comprising sound processor circuitry configured to optically transmit data and/or power to the cochlear implant circuitry; and
    an optical connector assembly configured to facilitate removable coupling of the implantable sound processor module to the cochlear implant module by way of the optical connector assembly;
    wherein the optical connector assembly comprises one or more optical fibers configured to facilitate the optical transmission of the data and/or the power from the sound processor circuitry to the cochlear implant circuitry while the implantable sound processor module is removably coupled to the cochlear implant module by way of the optical connector assembly; and
    wherein the sound processor circuitry optically transmits the data and/or the power to the cochlear implant circuitry by way of the one or more optical fibers while the implantable sound processor module is removably coupled to the cochlear implant module by way of the optical connector assembly.

2. The system of claim 1, wherein the optical connector assembly further comprises:
    a cable that houses the one or more optical fibers; and a modular connector disposed at a distal end of the cable.

3. The system of claim 2, wherein:
the modular connector is configured to removably connect to the cochlear implant module; and
the cochlear implant module further comprises an optical feedthrough assembly that optically connects the one or more optical fibers to the cochlear implant circuitry while the modular connector is removably connected to the cochlear implant module.

4. The system of claim 3, wherein a proximal end of the cable is permanently coupled to the implantable sound processor module.

5. The system of claim 4, wherein the implantable sound processor module further comprises an optical feedthrough assembly that optically connects the one or more optical fibers to the sound processor circuitry.

6. The system of claim 2, wherein:
the modular connector is configured to removably connect to the implantable sound processor module; and
the implantable sound processor module further comprises an optical feedthrough assembly that optically connects the one or more optical fibers to the cochlear implant circuitry while the modular connector is removably connected to the implantable sound processor module.

7. The system of claim 6, wherein a proximal end of the cable is permanently coupled to the cochlear implant module.

8. The system of claim 7, wherein the cochlear implant module further comprises an optical feedthrough assembly that optically connects the one or more optical fibers to the cochlear implant circuitry.

9. The system of claim 1, wherein the optical connector assembly further comprises:
a cable that houses the one or more optical fibers;
a first modular connector disposed at a proximal end of the cable; and
a second modular connector disposed at a distal end of the cable;
wherein the first modular connector is configured to removably connect to the cochlear implant module and wherein the second modular connector is configured to removably connect to the implantable sound processor module.

10. The system of claim 1, wherein the one or more optical fibers are further configured to facilitate optical transmission of data from the cochlear implant circuitry to the sound processor circuitry while the implantable sound processor module is removably coupled to the cochlear implant module by way of the optical connector assembly.

11. The system of claim 1, further comprising an implantable antenna configured to be implanted within the patient, wherein the optical connector assembly is further configured to facilitate removable coupling of the implantable antenna in place of the implantable sound processor module to the cochlear implant module.

12. The system of claim 1, further comprising an implantable battery configured to be implanted within the patient and to be communicatively coupled to the sound processor circuitry, wherein the implantable battery supplies the power that is optically transmitted to the cochlear implant circuitry.

13. The system of claim 12, wherein the implantable battery is separate from the implantable sound processor module and configured to be communicatively coupled to the sound processor module circuitry by way of a power link.

14. The system of 12, wherein the implantable sound processor module houses the implantable battery.

15. A system comprising:
a cochlear implant module configured to be implanted within a patient and comprising cochlear implant circuitry configured to apply electrical stimulation representative of one or more audio signals to the patient; and
an optical connector assembly coupled to the cochlear implant module and configured to be removably connected to an implantable sound processor module that comprises sound processor circuitry;
wherein the optical connector assembly comprises:
a modular connector configured to be removably connected to the implantable sound processor module, and
a cable permanently connected to the modular connector and that includes one or more optical fibers configured to facilitate optical transmission of data and power from the sound processing circuitry to the cochlear implant circuitry while the implantable sound processor module is removably connected to the modular connector; and
wherein the cochlear implant circuitry optically receives the data and the power from the sound processor circuitry by way of the one or more optical fibers while the implantable sound processor module is removably connected to the modular connector.

16. The system of claim 15, wherein the cochlear implant module further comprises an optical feedthrough assembly that optically connects the one or more optical fibers to the cochlear implant circuitry.

17. The system of claim 15, wherein the modular connector is disposed at a distal end of the cable.

18. A system comprising:
an implantable sound processor module configured to be implanted within a patient and comprising sound processor circuitry configured to optically transmit data and power; and
an optical connector assembly coupled to the sound processor module and configured to be removably connected to a cochlear implant module configured to be implanted within the patient and comprising cochlear implant circuitry configured to apply electrical stimulation representative of one or more audio signals to the patient;
wherein the optical connector assembly comprises:
a modular connector configured to be removably connected to the cochlear implant module, and
a cable that includes one or more optical fibers configured to facilitate receipt by the cochlear implant circuitry of the optically transmitted data and power from the sound processing circuitry while the cochlear implant module is removably connected to the modular connector; and
wherein the sound processor circuitry optically transmits the data and the power to the cochlear implant circuitry by way of the one or more optical fibers while the cochlear implant module is removably connected to the modular connector.

19. The system of claim 18, wherein the implantable sound processor module further comprises an optical feedthrough assembly that optically connects the one or more optical fibers to the sound processor circuitry.

20. The system of claim 18, wherein the modular connector is disposed at a distal end of the cable.

\* \* \* \* \*